US00PP22760P2

(12) United States Plant Patent
Wood

(10) Patent No.: US PP22,760 P2
(45) Date of Patent: May 29, 2012

(54) ***COTONEASTER* PLANT NAMED 'GERALD'**

(50) Latin Name: *Cotoneaster procumbens*
Varietal Denomination: Gerald

(75) Inventor: Timothy D. Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 207 days.

(21) Appl. No.: 12/798,017

(22) Filed: Mar. 27, 2010

(51) Int. Cl.
*A01H 5/00* (2006.01)

(52) U.S. Cl. ..... Plt./226

(58) Field of Classification Search ..... Plt./226
See application file for complete search history.

(56) References Cited

U.S. PATENT DOCUMENTS

PP16,230 P3 * 1/2006 Bellenot-Kapusta et al. Plt./226

OTHER PUBLICATIONS

UPOV ROM GTITM Computer Database, GTI Jouve Retrieval Software 2011/05 Citation for 'Gerald'.*
Anonymous. "Cotoneaster procumbens 'Little Dipper ('Gerald')'" Vite. Greenhouses available at http://www.vitegreenhouss.com/PlantDetail.asp?PlantID=S2010004 accessed Jul. 13, 2011.*
Anonymous TESS Record U.S. Trademark Resgistration No. 3670440 Aug. 18, 2009.*
Anonymous. Plant Varities Journal Oct. 2008/No. 69 see p. 20.*

* cited by examiner

*Primary Examiner* — Wendy C Haas
(74) *Attorney, Agent, or Firm* — C. A. Whealy

(57) ABSTRACT

A new and distinct cultivar of *Cotoneaster* plant named 'Gerald', characterized by its uniform and low mounding plant habit; moderately vigorous growth habit; freely branching habit; dark green-colored leaves; and good garden performance.

2 Drawing Sheets

Botanical designation: *Cotoneaster procumbens.*
Cultivar denomination: 'GERALD'.

BACKGROUND OF THE INVENTION

The present invention relates to a new and distinct cultivar of *Cotoneaster* plant, botanically known as *Cotoneaster procumbens* and hereinafter referred to by the name 'Gerald'.

The new *Cotoneaster* plant is a product of a planned breeding program conducted by the Inventor in Grand Haven, Mich. The objective of the breeding program is to develop new mounding and freely branching *Cotoneaster* plants with attractive foliage.

The new *Cotoneaster* plant originated from an open-pollination in 2001 of *Cotoneaster procumbens* 'Queen of Carpets', not patented, as the female, or seed, parent with an unknown selection of *Cotoneaster procumbens,* as the male, or pollen, parent. The new *Cotoneaster* plant was discovered and selected by the Inventor in 2005 as a single flowering plant within the progeny of the stated open-pollination in a controlled environment in Grand Haven, Mich.

Asexual reproduction of the new *Cotoneaster* plant by softwood cuttings in a controlled greenhouse environment in Grand Haven, Mich. since June, 2006 has shown that the unique features of this new *Cotoneaster* plant are stable and reproduced true to type in successive generations of asexual reproduction.

SUMMARY OF THE INVENTION

Plants of the new *Cotoneaster* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Gerald'. These characteristics in combination distinguish 'Gerald' as a new and distinct cultivar of *Cotoneaster:*

1. Uniform and low mounding plant habit.
2. Moderately vigorous growth habit.
3. Freely branching habit.
4. Dark green-colored leaves.
5. Good garden performance.

Plants of the new *Cotoneaster* can be compared to plants of the female parent, 'Queen of Carpets'. Plants of the new *Cotoneaster* differ from plants of 'Queen of Carpets' in the following characteristics:

1. Plants of the new *Cotoneaster* are more uniform in plant habit than plants of 'Queen of Carpets'.
2. Plants of the new *Cotoneaster* are more freely branching and denser than plants of 'Queen of Carpets'.

Plants of the new *Cotoneaster* can be compared to plants of *Cotoneaster microphyllus* 'Emerald Spray', not patented. Plants of the new *Cotoneaster* differ from plants of 'Emerald Spray' in the following characteristics:

1. Plants of the new *Cotoneaster* are lower growing than and not as upright as plants of 'Emerald Spray'.
2. Plants of the new *Cotoneaster* have larger and duller leaves than plants of 'Emerald Spray'.

BRIEF DESCRIPTION OF THE PHOTOGRAPHS

The accompanying colored photographs illustrate the overall appearance of the new *Cotoneaster* plant, showing the colors as true as it is reasonably possible to obtain in colored reproductions of this type. Colors in the photographs may differ slightly from the color values cited in the detailed botanical description which accurately describe the colors of the new *Cotoneaster* plant.

The photograph on the first sheet is a side perspective view (forefront of photograph) of typical plants of 'Gerald' grown in an outdoor nursery.

The photograph on the second sheet is a close-up view of a typical plant of 'Gerald'.

DETAILED BOTANICAL DESCRIPTION

The aforementioned photographs and following observations, measurements and values describe plants of the new *Cotoneaster* grown in an outdoor nursery in Grand Haven, Mich. during the spring and summer under conditions which closely approximate commercial *Cotoneaster* production. Plants were three years old when the photographs and the description were taken. In the description, color references are made to The Royal Horticultural Society Colour Chart, 1995 Edition, except where general terms of ordinary dictionary significance are used.

Botanical classification: *Cotoneaster procumbens* 'Gerald'.

Parentage:

*Female, or seed, parent.*—*Cotoneaster procumbens* 'Queen of Carpets', not patented.

*Male, or pollen, parent.*—Unknown selection of *Cotoneaster procumbens,* not patented.

Propagation:

*Type.*—By softwood cuttings.

*Time to initiate roots.*—About 40 days at 25° C.

*Time to produce a rooted young plant.*—About six months at 25° C.

*Root description.*—Fine to thick, fibrous.

*Rooting habit.*—Freely branching; dense.

Plant description:

*Plant form and growth habit.*—Perennial shrub; uniform and low-mounding plant habit; moderately vigorous growth habit.

*Branching habit.*—Freely branching habit with about numerous primary lateral branches; pinching (removal of terminal apices) will enhance lateral branch development.

*Plant height.*—About 23 cm.

*Plant diameter* (*area of spread*).—About 65 cm.

Lateral branch description:

*Length.*—About 11 cm.

*Diameter.*—About 1.5 mm.

*Internode length.*—About 1 cm.

*Texture.*—Smooth, glabrous.

*Color.*—Close to 183A.

Foliage description:

*Arrangement.*—Alternate, simple.

*Length.*—About 1 cm to 1.5 cm.

*Width.*—About 5 mm to 10 mm.

*Shape.*—Rounded.

*Apex.*—Obtuse.

*Base.*—Obtuse.

*Margin.*—Entire.

*Texture, upper and lower surfaces.*—Smooth, glabrous.

*Venation pattern.*—Pinnate.

*Color.*—Developing leaves, upper surface: Close to 144A. Developing leaves, lower surface: Close to 146C. Fully expanded leaves, upper surface: Close to 137B; venation, close to 137B. Fully expanded leaves, lower surface: Close to 138B; venation, close to 138B.

*Petiole.*—Length: About 4 mm. Diameter: About 1 mm. Texture, upper and lower surfaces: Smooth, glabrous. Color, upper and lower surfaces: Close to 152D.

Flower description: Flower initiation and development have not been observed on plants of the new *Cotoneaster.*

Garden performance: Plants of the new *Cotoneaster* have been observed to have good garden performance and to tolerate rain, wind and temperatures ranging from about −27° C. to about 34° C.

Pathogen/pest resistance: Plants of the new *Cotoneaster* have not been observed to be resistant to pathogens and pests common to *Cotoneaster.*

It is claimed:

1. A new and distinct *Cotoneaster* plant named 'Gerald' as illustrated and described.

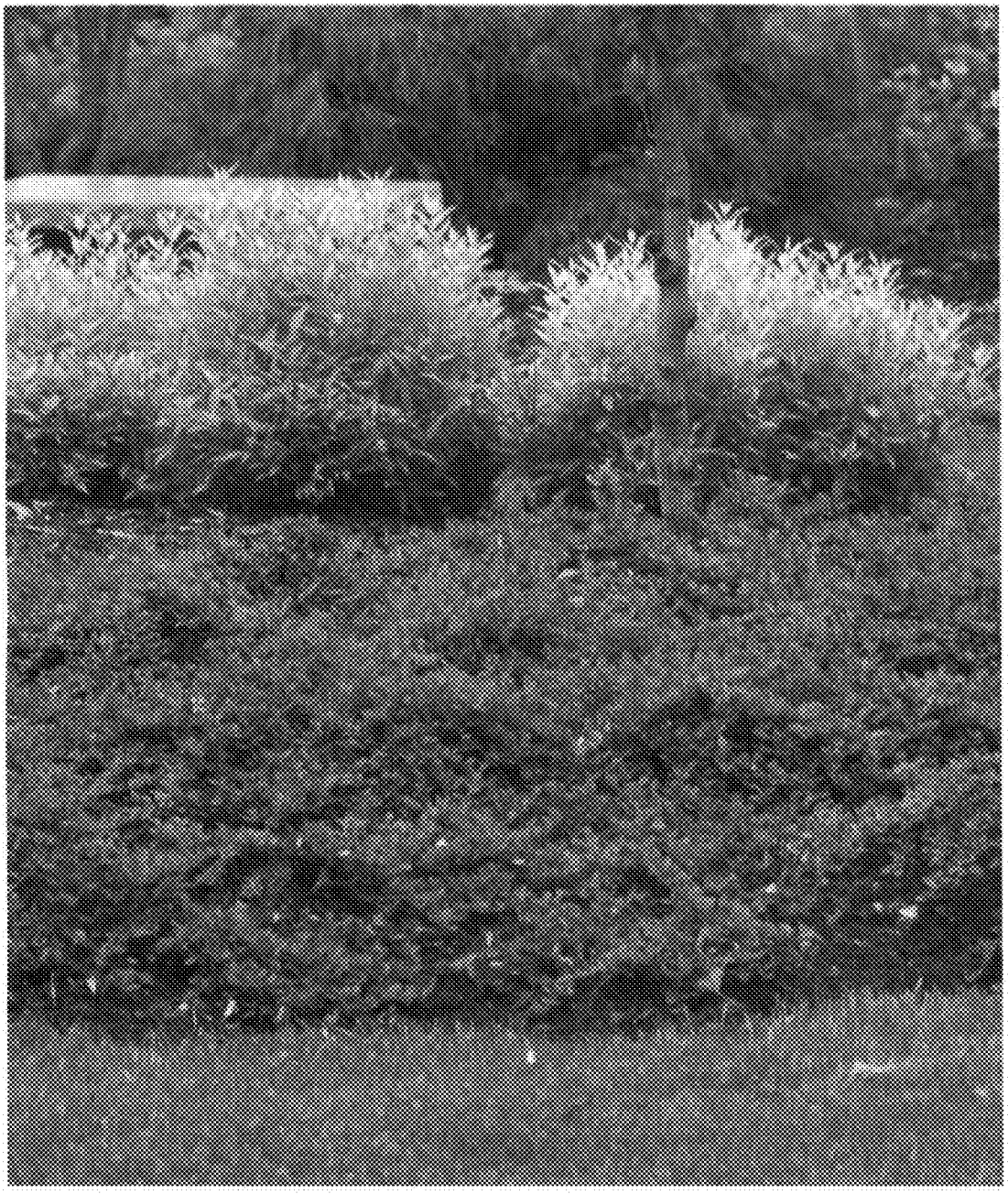

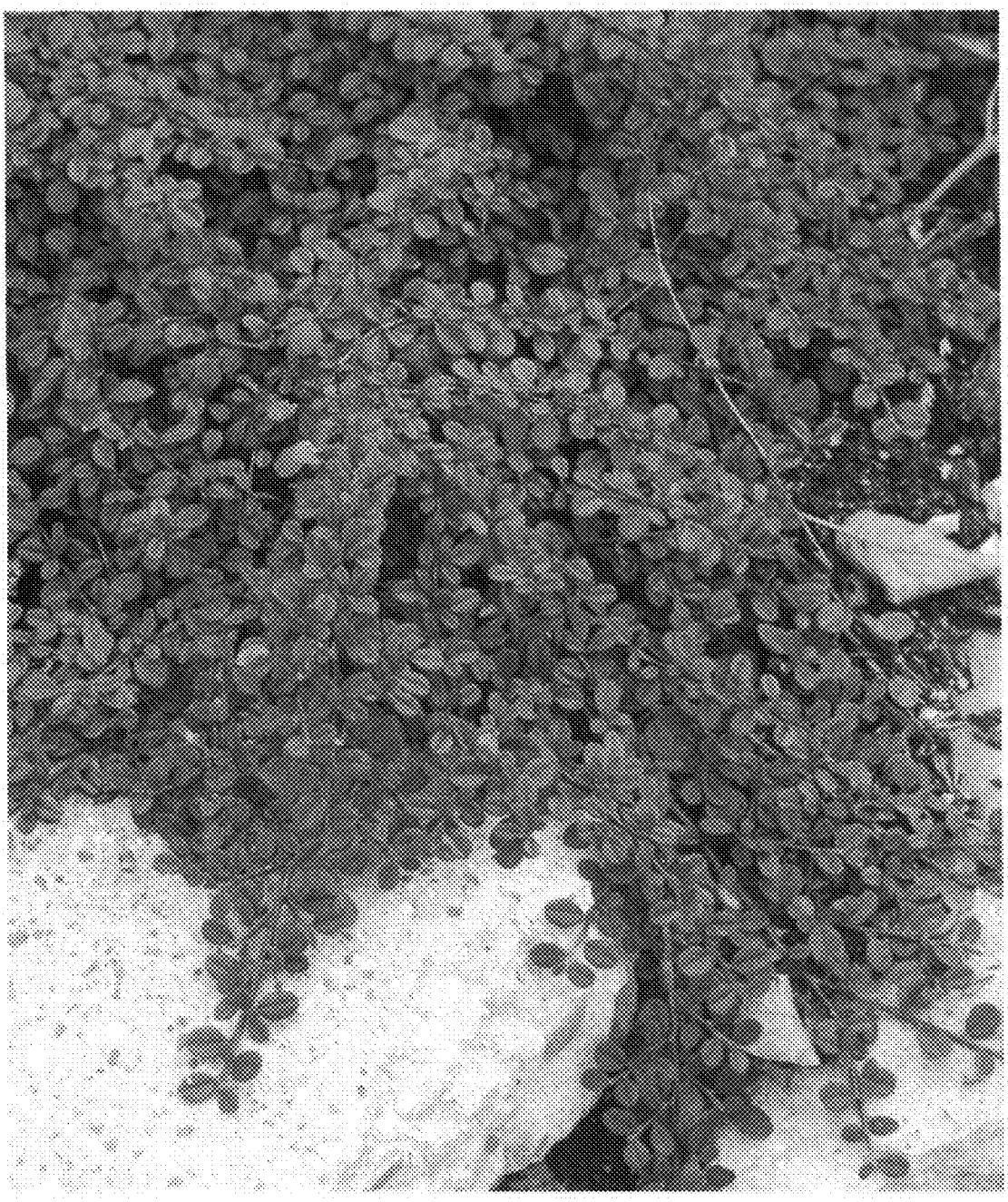

* * * * *